(12) United States Patent
Soerensen et al.

(10) Patent No.: US 7,993,890 B2
(45) Date of Patent: Aug. 9, 2011

(54) HYDROLYSIS OF ARABINOXYLAN

(75) Inventors: Hanne Risbjerg Soerensen, Holte (DK); Sven Pedersen, Gentofte (DK); Anders Viksoe-Nielsen, Slangerup (DK); Christel Thea Joergensen, Lyngby (DK); Lars Hylling Christensen, Alleroed (DK); Christian Isak Joergensen, Bagsvaerd (DK); Carsten Hoerslev Hansen, Copenhagen (DK); Lene Venke Kofod, Uggerloese (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 11/909,280

(22) PCT Filed: Apr. 25, 2006

(86) PCT No.: PCT/DK2006/000214

§ 371 (c)(1),
(2), (4) Date: Sep. 21, 2007

(87) PCT Pub. No.: WO2006/114095

PCT Pub. Date: Nov. 2, 2006

(65) Prior Publication Data

US 2008/0274527 A1 Nov. 6, 2008

Related U.S. Application Data

(60) Provisional application No. 60/676,115, filed on Apr. 29, 2005, provisional application No. 60/735,661, filed on Nov. 10, 2005, provisional application No. 60/738,651, filed on Nov. 21, 2005.

(30) Foreign Application Priority Data

Apr. 26, 2005 (DK) .................................. 2005 00609
Nov. 10, 2005 (DK) .................................. 2005 01562
Nov. 18, 2005 (DK) .................................. 2005 01612

(51) Int. Cl.
*C12P 7/06* (2006.01)
*C12N 11/18* (2006.01)
*C12N 9/99* (2006.01)
*C12N 9/24* (2006.01)
*C12N 1/20* (2006.01)
*C12N 15/00* (2006.01)
*C07H 21/04* (2006.01)

(52) U.S. Cl. ........ 435/161; 435/175; 435/183; 435/200; 435/252.3; 435/320.1; 536/23.2

(58) Field of Classification Search .................... None
See application file for complete search history.

(56) References Cited

U.S. PATENT DOCUMENTS
7,090,973 B1 8/2006 Breton

FOREIGN PATENT DOCUMENTS
WO WO 96/06935 3/1996

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Seffernick et al. J Bacteriol. Apr. 2001; 183 (8): 2405-10.*
Sorensen et al. Biotechnol Bioeng. Mar. 20, 2003;81(6):726-31.*
Faulds et al. (Appl Microbiol Biotechnol. Dec. 2002;60(4):489-94. Epub Oct. 12, 2002.*
Soerensen et al. Appl Microbiol Biotechnol. Dec. 2006;73(4):850-61. Epub Aug. 30, 2006.*
Sorensen et al., Appl. Microbiol Biotechnol, vol. 73, pp. 850-861 (2006).
Sorensen et al., Enzyme and Microbial Technology, vol. 36, pp. 773-784 (2005).
Sorensen et al., Biotechnology and Bioengineering, vol. 81, No, 6, pp. 726-731 (2003).
Adelsberger et al., Microbiology, vol. 150, pp. 2257-2266 (2004).
van den Brock et al., Applied Microbial Biotechnology, vol. 67, pp. 641-647 (2005).
Sunna et al., Critical Reviews in Biotechnology, vol. 17. pp. 39-67 (1997).
Van Laere et al., Applied Microbiol Biotechnology, vol. 47, pp. 231-235 (1997).
Nogawa et al., Applied and Environmental Microbiology, vol. 65, No. 9, pp. 3964-3968 (1999).
Ferre et al., European Journal of Biochemistry, vol. 267, pp. 6633-6641 (2000).
Unitika Ltd., Abstract of JP 2004033002 (2004).
Unitika Ltd., Abstract of JP 2006050996 (2006).
International Search Report received in PCT/DK2006/000214, (2006).
Van Laere et al, Applied Microbiology and Biotechnology, vol. 51, pp. 606-613, (1999).
Wells, Biochemistry, vol. 29, No. 37, pp. 8509-8517 (1990).
Beylot et al., Biochem. J., vol. 358, pp. 607-614 (2001).

* cited by examiner

*Primary Examiner* — Christian Fronda
(74) *Attorney, Agent, or Firm* — Elias Lambiris

(57) ABSTRACT

The present invention relates to a process for enzymatic hydrolysis of arabinoxylan, and an enzyme composition suitable for use in such a process.

28 Claims, 1 Drawing Sheet

A

B

C

A

B

C

HYDROLYSIS OF ARABINOXYLAN

CROSS-REFERENCE TO RELATED APPLICATIONS

This application is a 35 U.S.C. 371 national application of PCT/DK2006/000214 filed Apr. 25, 2006, which claims priority or the benefit under 35 U.S.C. 119 of Danish application nos. PA 2005 00609, PA 2005 01562 and PA 2005 01612 filed Apr. 26, 2005, Nov. 10, 2005 and Nov. 18, 2005, respectively, and U.S. provisional application Nos. 60/676,115, 60/735,661 and 60/738,651 filed Apr. 29, 2005, Nov. 10, 2005, and Nov. 21, 2005, respectively, the contents of which are fully incorporated herein by reference.

SEQUENCE LISTING

The present invention comprises a sequence listing.

FIELD OF THE INVENTION

The present invention relates to a process for enzymatic hydrolysis of arabinoxylan, and an enzyme composition suitable for use in such a process.

BACKGROUND OF THE INVENTION

Arabinoxylan, a polysaccharide composed of xylose and arabinose, is part of the water soluble and insoluble fibre present in cereals, in particular in the cell walls. Hydrolysis of arabinoxylan is an important prerequisite for improved utilization of cereal hemicellulose, e.g. in the ethanol fermentation industry and other cereal-based industries.

Arabinoxylan consist of alpha-L-arabinofuranose residues attached as branch-points to a beta-(1-4)-linked xylose polymeric backbone. The xylose residues may be mono-substituted in the C2- or C3-position or di-substituted at both the C2- and C3-position. In addition, ferulic acid and p-coumaric acid may be covalently linked to arabinoxylan via esterification at the C5 position of some of the arabinosyl units. These substitutions on the xylan backbone retard the actions of xylanases and the complete hydrolysis of arabinoxylan thus requires both side-group cleaving and depolymerising activities. The major products of hydrolysis of arabinoxylan are the C5 sugars xylose and arabinose.

A process for hydrolysis of arabinoxylan using synergistic interactions amongst enzymes present commercial enzyme compositions from *Humicola insolens* and *Trichoderma reesei* has previously been described by the present inventors in Sørensen, H. R. et al. (Biotechnology and Bioengineering, Vol. 81, No. 6, March 20, 726-731, 2003). Enzyme catalyzed hydrolysis of >50% of the soluble part of the wheat endosperm arabinoxylan could be achieved, but only low monosaccharide yields were obtained with similar enzymatic treatments on insoluble wheat arabinoxylan. However, since the arabinoxylan degrading enzyme activities are present as side-activities in commercial preparations having other enzyme activities as their main activity, high dosage levels of 5-10 wt % of the enzyme preparation per weight of the substrate has to be added for obtaining efficient hydrolysis. Such high enzyme addition levels are not feasible for use in full scale production applications and improved processes for hydrolysis of arabinoxylan are thus needed.

SUMMARY OF THE INVENTION

The inventors have now found improved processes for hydrolysis of arabinoxylan and an enzyme composition suitable for use in such a process. In the process of the invention an arabinoxylan containing substrate is contacted with an enzyme having activity towards di-substituted xyloses, e.g. such as an alpha-L-arabinofuranosidase of Glycoside Hydrolase Family 43 (GH43), and an enzyme having activity towards C2- or C3-position mono-substituted xyloses, e.g. such as an alpha-L-arabinofuranosidase of Glycoside Hydrolase Family 51, 54 or 62 (GH51, GH54 or GH62).

Accordingly the invention provides in a first aspect a process comprising adding to an arabinoxylan containing substrate an enzyme having activity towards di-substituted xyloses, and, an enzyme having activity towards C2- or C3-position mono-substituted xyloses.

The invention provides in a second aspect a composition for hydrolysis of arabinoxylan said composition comprising an enzyme having activity towards di-substituted xyloses, and, an enzyme having activity towards C2- or C3-position mono-substituted xyloses.

The invention provides in further aspects uses of the composition of the second aspect.

BRIEF DESCRIPTION OF THE DRAWING

FIG. 1A shows intact arabinoxylan. Arabinofuranosyl residues linked alpha(1→3) (mono-substituted) and alpha(1→2) and alpha(1→3) (di-substituted) to internal xyloses.

FIG. 1B shows di-substituted arabinoxylan. Arabinofuranosyl residues linked alpha(1→2) and alpha(1→3) (di-substituted) to internal xyloses.

FIG. 1C shows singly substituted arabinoxylan. Arabinofuranosyl residues linked alpha(1→2) and alpha(1→3) (mono-substituted) to internal xyloses

FIG. 2A shows arabinosyl groups linked to internal C-3. Arabinofuranosyl residues linked alpha(1→3) (mono-substituted) and alpha(1→2) and alpha(1→3) (di-substituted) to internal xyloses.

FIG. 2B shows arabinosyl groups linked to terminal C-3. Arabinofuranosyl residues linked alpha(1→3) (mono-substituted) to terminal xyloses and alpha(1→2) and alpha(1→3) (di-substituted) to internal xyloses FIG. 2C shows arabinosyl groups linked to internal C-2. Arabinofuranosyl residues linked alpha(1→2) and alpha (1→3)(mono-substituted) to internal xyloses

DETAILED DESCRIPTION OF THE INVENTION

Figure 1:
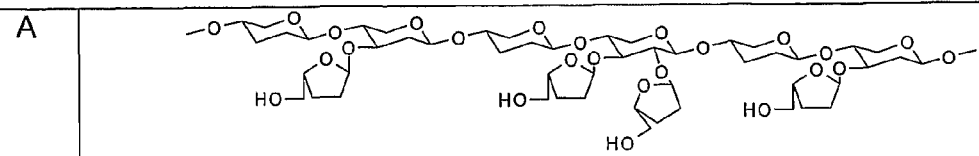
FIG. 1A-C show arabinoxylan polymers.
Figure 1:
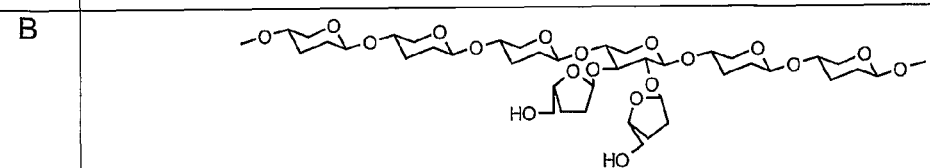
Figure 1:
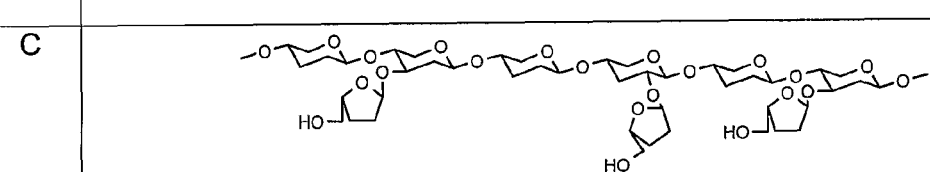
Figure 2:
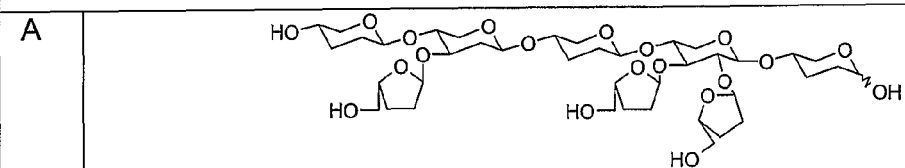
FIG. 2A-C show arabinoxylo-oligosaccharides.
Figure 2:
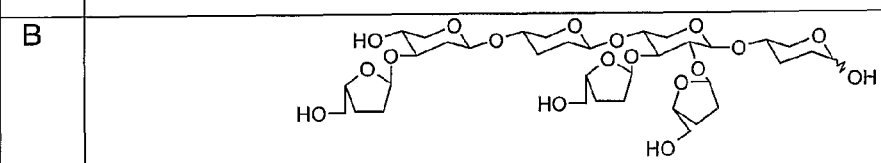
Figure 2:
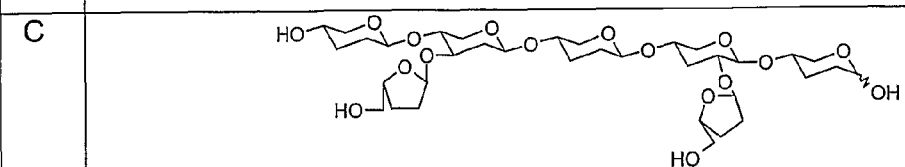

In the description and claims which follows the following are definitions of some of the technical terms which are employed.

The numbering of Glycoside Hydrolase Families applied in this disclosure follows the concept of Coutinho, P. M. & Henrissat, B. (1999) *CAZy—Carbohydrate-Active Enzymes server* at URL: http://afmb.cnrs-mrs.fr/~cazy/CAZY/index.html or alternatively Coutinho, P. M. & Henrissat, B. 1999; The modular structure of cellulases and other carbohydrate-active enzymes: an integrated database approach. In "*Genetics, Biochemistry and Ecology of Cellulose Degradation*", K. Ohmiya, K. Hayashi, K. Sakka, Y. Kobayashi, S. Karita and T. Kimura eds., Uni Publishers Co., Tokyo, pp. 15-23, and Bourne, Y. & Henrissat, B. 2001; Glycoside hydrolases and glycosyltransferases: families and functional modules, *Current Opinion in Structural Biology* 11:593-600.

The term "granular starch" in context of the present invention is understood as raw uncooked starch, i.e. starch that has not been subjected to a gelatinization.

The term "biomass" means in context of the present invention all hemicellulose containing materials. Biomass is a very heterogeneous and chemically complex resource comprising byproducts from agricultural and industrial processing of all forms of plant material. The biomass may be any plant-derived organic matter including herbaceous and woody energy crops, agricultural food and feed crops, agricultural crop waste and residues such as straw, stalks, leaves, corn bran, husks, cobs, rind, shells, and pods, wood waste such as bark, shavings, sawdust, wood pulp and pulping liquor. The biomass may include biomass from waste, such as waste paper, cardboard, construction and demolition wood waste. The biomass may also include sludge or solids recovered from industrial or municipal waste water treatment as well as from animal manure.

The "arabinoxylan containing substrate" to be treated in the process of the present invention may be obtained from any vegetable source, in particular be obtained from tubers, roots, stems, legumes, cereals or whole grain. Preferred are hemicellulose containing agricultural waste products (i.e. residues and/or by-products) such as cassava peels, cocoa pods, rice husks and/or hulls, rice bran from rice polishing, cobs, straw, hulls and/or husks from cereal grain, pressed sugar cane stalk, sugar beet pulp, locust bean pulp or other vegetable or fruit pomaces. The substrate may be any biomass.

Preferred is a substrate obtained from cereal grain, e.g. such as milled grain or by-products from processing of cereal grain, e.g. an arabinoxylan containing by-product from wet- or dry-milling of cereal, The cereal grain may be any cereal grain though preferred is a cereal grain selected from the group consisting of corn (maize), wheat, barley, oat, rice, sorghum and millet. Most preferred for the present invention is an arabinoxylan containing substrate derived from wheat.

The arabinoxylan containing substrate may be the grist or mash of a brewing and/or fermentation process, or it may be a by-product from a brewing and/or fermentation process, e.g. wet or dried distillers grain, spent grain, vinasse, bagasse etc.

Arabinoxylan containing substrates usually comprise both water soluble and water in-soluble arabinoxylan. Contemplated for the aspects of the present invention is substrates comprising both water soluble arabinoxylan and/or water in-soluble arabinoxylan.

Processes

The process of the first aspect wherein an arabinoxylan containing substrate with enzyme activities comprising an enzyme having activity towards di-substituted xyloses, and an enzyme having activity towards C2- or C3-position mono-substituted xyloses is particular suitable for the production of linear xylose polymers (xylan homopolymer) with little or no arabinose side groups. In a preferred embodiment the enzyme having activity towards di-substituted xyloses is an alpha-L-arabinofuranosidase of GH43, and an enzyme having activity towards C2- or C3-position mono-substituted xyloses is an alpha-L-arabinofuranosidase of GH51, GH54 or/or GH62, more preferably a GH51.

When the two arabinofuranosidases are added to an arabinoxylan solution the resulting products will be high molecular weight linear xylose polymers and arabinose molecules. This will allow for an easy separation of the linear xylose polymer by known techniques (ultrafiltration or solvent precipitation of the xylan in an ethanol solution) from arabinose.

The linear xylose polymers may be further partially digested with enzyme activities, such as a beta-xylosidase, and/or an endo-1,4-beta-xylanase, to yield xylo-oligosaccharides, which also have dietary applications. Preferably the beta-xylosidase is a beta-xylosidase of GH3, and/or preferably the endo-1,4-beta-xylanase is an endo-1,4-beta-xylanase of GH10 or GH11.

When an endo-1,4-beta-xylanase is added to the purified linear xylose polymers (purified as described above) the resulting products will be xylo-oligosaccharides essentially free of arabinose side groups. The size of the oligosaccharides can be controlled by the dose of the endo-1,4-beta-xylanase as well as by the length of the reaction time.

When both an endo-1,4-beta-xylanase and a beta-xylosidase are added to the purified linear xylose polymers the resulting product will be xylose.

Thus the invention provides a process for obtaining a linear xylose polymer product essentially free of arabinose substituents, a process for obtaining a xylo-oligosaccharide product essentially free of arabinose side groups and a process for separating xylose and arabinose in a simpler way than previous technology (ion exchange chromatography).

Furthermore the invention provides a linear xylose polymer product of high molecular weight and essentially free of arabinose side groups and a xylo-oligosaccharide product essentially free of arabinose side groups.

Preferably the linear xylose polymer product or xylo-oligosaccharide product comprises at least 50%, at least 60%, at least 70%, at least 90%, at least 80%, at least 90%, at least 95%, such as at least 98% polymer by weight of the product which polymer has a degree of polymerization of at least 3, at least 4, at least 5, at least 6, at least 7, at least 8, at least 9, at least 10, at least 15, at least 20, at least 25, at least 30, at least 35, at least 40, at least 50, at least 60, at least 70, at least 80, at least 90, at least 100, at least 120 at least 150, at least 200, at least 300, at least 500, at least 1000, at least 2000, at least 5000, or at least 10000.

Preferably the linear xylose polymer product or xylo-oligosaccharide product comprising at least 50%, at least 60%, at least 70%, at least 90%, at least 80%, at least 90%, at least 95%, such as at least 98% polymer by weight of the product which polymer has a degree of polymerization of at of less than 5000, less than 2500, less than 1500, less than 1000, less than 500, less than 100, less than 75, less than 50, less than 25, less than 10, less than 9, less than 8, less than 7, less than 6, less than 5, and preferably less than 4.

Preferably the linear xylose polymer product or xylo-oligosaccharide product comprises at least 50%, at least 60%, at least 70%, at least 90%, at least 80%, at least 90%, at least 95%, such as at least 98% polymer by weight of the product which polymer has a degree of polymerization selected from the group consisting of the intervals from 3 to 10, from 11 to 25, from 26 to 50, from 51 to 100, from 101 to 200, from 201 to 500, from 501 to 1000, from 1001 to 5000, and from 5001 to 10000.

The linear xylose polymers produced may be used as a food additive, e.g. as a bulking agent, a low calorie fat replacer or dietary fiber, such as a non soluble dietary fibre. Applications will e.g. be in cakes, extruded snacks, other cereal products, and confectionary. Technical applications will include additive to paper and pulp products, plastic materials (films), where plasticizers might be added, and as a sizing agent.

The xylo-oligosaccharide product will have applications as dietary fibres, such as soluble dietary fibres. These dietary fibres may be used for increasing the amount of bifidus-bacteria in the lower gut. Applications will e.g. be in yoghurt, ice cream, and soft drinks.

An embodiment of the first aspect, wherein further enzyme activities are present, such as a beta-xylosidase of GH3, and/or an endo-1,4-beta-xylanase of GH10 is particularly useful when more complete hydrolysis of arabinoxylan is wanted.

Apart from releasing C5 sugars the hydrolysis of arabinoxylan also makes associated glucose polymers such as starch and cellulase more accessible for the action of the appropriate enzymes. This is particularly useful when degradation of complex substrates are required, e.g. in brewing or in hydrolysis of starch or biomass for fuel ethanol production, or in animal feed composition.

Xylose and/or arabinose released during enzymatic hydrolysis of arabinoxylan in the process of the first aspect and/or second aspect may be used as a source of xylose and/or arabinose as such, or as raw material for chemical/enzymatic synthesis or fermentation processes, e.g. for production of xylitol, xylaric acid, xylonic acids, arabonic acid, arabinoic acid, 2,3-butanediol, lactic acid, lactonic acid, furans and/or ethanol.

For degradation of even more complex substrates, or where a more complete degradation is required, the presence of even further enzyme activities may be desired. In a preferred embodiment the enzyme activity/activities further comprise an acetyl xylan esterase (EC 3.1.1.72) and/or a feruloyl esterase (EC 3.1.1.73) and/or an alpha-glucuronidiase (EC 3.2.1.139).

In an embodiment of the process of the first aspect the enzyme activity/activities further comprise an enzyme selected from the list consisting of an acetyl xylan esterase, a feruloyl esterase, an alpha-amylase, a glucoamylase, a phytase and a protease.

In brewing and other fermentation processes based on cereal grist arabinoxylans can be extracted from cell walls with hot water and may form solutions of high viscosity. If in brewing processes malts are used which are not adequately modified during malting, malt extracts can contain high levels of arabinoxylans and other polysaccharides causing an increase in viscosity of the extracts. The difficulties associated with the filtration of such extracts can significantly slow down the brewing process. In an embodiment of the present invention the arabinoxylan containing substrate to be contacted with the composition of the invention is a mash of a beer brewing process, whereby e.g. the viscosity of the mash is reduced and/or further polysaccharides released.

In an embodiment of the present invention the process is any ethanol process, based on enzymatic hydrolysis of gelatinized or granular starch, e.g. on granular starch as described in WO2004080923 or WO2004081193. By contacting the mash with the composition of the invention the viscosity of the mash may be reduced. Also further polysaccharides may be released, not only as C5 sugars but also as glucose when the break-down of arabinoxylan leaves the starch more accessible to amyloytic enzymes usually present during such processes. An additional enzyme which advantageously may be applied in a starch-based ethanol process is an enzyme selected from the list consisting of beta-glucanase, alpha-amylase, glucoamylase, CGTase, phytase and protease.

The process of present invention may be any ethanol process, comprising enzymatic hydrolysis of biomass and/or effluent from pre-treatment of biomass. An additional enzyme which advantageously may be applied in a biomass-based ethanol process is an enzyme selected from the list consisting of beta-glucanase, cellulase, cellobiohydrolase, and beta-glucosidase.

In a fermentation process the arabinoxylan hydrolysate may advantageously be contacted with a yeast or another fermenting organism capable of utilizing C5 sugars. Alternatively, the arabinoxylan hydrolysate may be contacted with a xylose isomerase (EC 5.3.1.5) for isomerization of xylose into xylulose which is fermentable to ethanol using a *Saccharomyces* yeast.

The composition of the invention may also be used in processing of a cereal raw material intended for use as a feed/food product or the composition may be applied as a feed/food additive. Such enzyme-based feed/food additives can be incorporated into a cereal-based feed/food product which includes one or more of wheat, barley, triticale, rye, rice and corn. The feed/food additive has the advantage of improving the feed/food conversion ratio and/or increasing the digestibility of the cereal-based feed/food product in which it is included. The composition of the invention used as feed/food additive may preferably be used together with a phytase.

The present invention furthermore relates to composition for treating an arabinoxylan containing substrate, said composition comprising an enzyme having activity towards di-substituted xyloses, e.g. such as an alpha-L-arabinofuranosidase of GH43, and an enzyme having activity towards C2- or C3-position substituted xyloses, e.g. such as an alpha-L-arabinofuranosidase of GH51, GH54 or GH62.

The present invention further relates to compositions comprising an alpha-L-arabinofuranosidase of GH43, an alpha-L-arabinofuranosidase of GH51, GH54 or GH62, a beta-xylosidase, and/or an endo-1,4-beta-xylanase, as well as to composition comprising the aforementioned activities and an enzyme selected from the group consisting of alpha-amylase, CGTase, glucoamylase, phytase, protease, beta-glucanase, cellulase, cellobiohydrolase, and/or beta-glycosidase.

The composition may comprise alpha-L-arabinofuranosidase of GH43 in an amount of at least 5%, at least 10%, at least 15%, at least 20%, at least 25%, at least 30%, at least 40%, at least 50%, at least 70%, or even at least 80% w/w of total arabinofuranosidase enzyme protein present in the composition. More preferably the composition may comprise alpha-L-arabinofuranosidase of GH43 in an amount of at least 5%, such as at least 10% at least 15%, at least 20%, at least 25%, at least 30%, at least 40%, at least 50%, at least 70% w/w of total enzyme protein present in the composition.

The composition may be used for treatment of an arabinoxylan containing substrate, e.g. in a fermentation process, e.g. for reduction of viscosity of a slurry and/or solution comprising an arabinoxylan containing substrate. The composition may be used for producing a feed/food product, e.g. for producing or modifying a nutritional/dietary fibre and/or for producing a xylose, arabinose and/or linear xylose or for producing derivatives of xylose, arabinose by fermentation, enzymatic processing or chemical synthesis.

The invention furthermore provides a process wherein an arabinoxylan containing substrate and/or a biomass is contacted with an enzyme arabinofuranosidase capable of releasing arabinose from di-substituted xyloses. Preferably the enzyme capable of releasing arabinose from di-substitued xyloses is an arabinofuranosidase. Preferably the alpha-L-arabinofuranosidase is an alpha-L-arabinofuranosidase of GH43. The alpha-L-arabinofuranosidase of GH43 is preferably derived of bacterial, of fungal or of plant origin. Preferably the arabinoxylan containing substrate and/or the biomass is selected from the list consisting of herbaceous and/or woody energy crops, agricultural food and feed crops, animal feed products, tubers, roots, stems, legumes, cassava peels, cocoa pods, rice husks and/or hulls, rice bran, cobs, straw, hulls, husks, sugar beet pulp, locust bean pulp, vegetable pomaces, agricultural crop waste, straw, stalks, leaves, corn bran, husks, cobs, rind, shells, pods, wood waste, bark, shavings, sawdust, wood pulp, pulping liquor, waste paper, cardboard, wood waste, industrial or municipal waste water solids, manure, by-product from brewing and/or fermentation processes, wet distillers grain, dried distillers grain, spent grain, vinasse and bagasse.

Enzymes

Alpha-L-arabinofuranosidase Having Activity Towards Di-substituted Xyloses

The enzyme having activity towards di-substituted xyloses, e.g. such as an alpha-L-arabinofuranosidase of GH43, may be of microbial origin, e.g. derivable from a strain of a filamentous fungus (e.g., *Humicola, Aspergillus, Trichoderma, Fusarium, Penicillum*) or from a bacteria (e.g. *Bacillus, Bifidobacterium*). A suitable such enzyme may be selected by the assay for alpha-arabinofuranosidase activity on di-substituted arabinoxylan in the Methods section.

Preferably the alpha-L-arabinofuranosidase of GH43 is derived from *Humicola insolens*. Most preferably the alpha-L-arabinofuranosidase of GH43 is the polypeptide shown as SEQ ID NO:1, more preferably the polypeptide shown as amino acids 19-558 of SEQ ID NO:1, or even more preferably a polypeptide which has at least 75%, at least 85%, at least 90%, at least 95%, at least 96%, at least 97%, at least 98%, or at least 99% identity with the amino acid sequence shown as amino acids 1-540 of SEQ ID NO:1 (hereinafter "homologous polypeptides").

The alpha-L-arabinofuranosidase of GH43 may also derived from *Bifidobacterium adolescenti*. More preferably the alpha-L-arabinofuranosidase of GH43 is the enzyme described by Van Laere, 1997, in Appl. Microbiol. Biotechnol, 47, 231-235 and/or by Van den Broek, 2005, in Applied Microbiology and Biotechnology.

An enzyme having activity towards di-substituted xyloses, e.g. such as an alpha-L-arabinofuranosidase of GH43, may be added in amounts of 0.001-1.0 g/kg DM substrate, preferably in the amounts of 0.005-0.5 g/kg DM substrate, and most preferably from 0.05-0.10 g/kg DM substrate.

Alpha-L-arabinofuranosidase Having Activity Towards Mono-Substituted Xyloses

The enzyme having activity towards C2- and/or C3-position mono-substituted xyloses, e.g. such as an alpha-L-arabinofuranosidase of GH51, GH54 or GH62, may be of microbial origin, such as derivable from a strain of a filamentous fungus (e.g., *Meripilus, Humicola, Aspergillus, Trichoderma, Fusarium, Penicillum*) or from a bacteria (e.g. *Bacillus*). Preferably the enzyme is an alpha-L-arabinofuranosidase of GH51, and more preferably the alpha-L-arabinofuranosidase GH51 is derived from Meripilus giganteus. The polypeptide may preferably have at least 75%, at least 85%, at least 90%, at least 95%, at least 96%, at least 97%, at least 98%, or at least 99% identity with the amino acid sequence shown as amino acids 1-627 of SEQ ID NO:2 (hereinafter "homologous polypeptides"). More preferably the alpha-L-arabinofuranosidase is the polypeptide shown as SEQ ID NO:2, even more preferably the polypeptide shown as amino acids 17-643 of SEQ ID NO:2.

Alpha-L-arabinofuranosidase of GH51, GH54 or GH62 may be added in amounts of 0.001-1.0 g/kg DM substrate, preferably in the amounts of 0.005-0.5 g/kg DM substrate, and most preferably from 0.05-0.10 g/kg DM substrate Beta-xylosidase The beta-xylosidase of is preferably a beta-xylosidase of GH3. The beta-xylosidase may be of microbial origin, such as derivable from a strain of a filamentous fungus (e.g., *Trichoderma, Meripilus, Humicola, Aspergillus, Fusarium* or from a bacteria (e.g. *Bacillus*). Preferably the beta-xylosidase is a beta-xylosidase of GH3 derived from *Trichoderma reesei* and more preferably the beta-xylosidase of GH3 is the polypeptide shown as SEQ ID NO:3 or a polypeptide which has at least 75%, at least 85%, at least 90%, at least 95%, at least 96%, at least 97%, at least 98%, or at least 99% identity with the amino acid sequence of SEQ ID NO:3 (hereinafter "homologous polypeptides"). Beta-xylosidase of GH3 may be added in amounts of 0.001-1.0 g/kg DM substrate, preferably in the amounts of 0.005-0.5 g/kg DM substrate, and most preferably from 0.05-0.10 g/kg DM substrate Endo-1,4-beta-xylanase The endo-1,4-beta-xylanase is preferably an endo-1,4-beta-xylanase of GH10 or GH11. The endo-1,4-beta-xylanase may be of microbial origin, such as derivable from a strain of a filamentous fungus (e.g., *Trichoderma, Meripilus, Humicola, Aspergillus, Fusarium*) or from a bacteria (e.g. *Bacillus*). The endo-1,4-beta-xylanase is preferably an endo-1,4-beta-xylanase of GH10 derived from *Humicola insolens* and more preferably the endo-1,4-beta-xylanase of GH10 is the polypeptide shown as SEQ ID NO:4, more preferably as amino acids 17-389 of SEQ ID NO:4, or even more preferably a polypeptide which has at least 75%, at least 85%, at least 90%, at least 95%, at least 96%, at least 97%, at least 98%, or at least 99% identity with the amino acid sequence shown as amino acids 1-373 of SEQ ID NO:4 (hereinafter "homologous polypeptides").

Endo-1,4-beta-xylanase of GH10 may be added in amounts of 0.001-1.0 g/kg DM substrate, preferably in the amounts of 0.005-0.5 g/kg DM substrate, and most preferably from 0.05-0.10 g/kg DM substrate.

Materials and Methods

Enzymes Used

A GH43 alpha-L-arabinofuranosidase from *H. insolens* (SEQ ID NO:1), a GH51 alpha-L-arabinofuranosidase from *M. giganteus* (SEQ ID NO:2), a GH3 beta-xylosidase from *Trichoderma reesei* (SEQ ID NO:3) and a GH10 endo-1,4-beta-xylanase from *H. insolens* (SEQ ID NO:4). The aforementioned enzymes were cloned using basic molecular techniques (Ausubel et al., 2003, Curr. Prot. Mol. Biol., John Wiley & Sons, Cambridge, USA, Christgau et al. 1995, Curr. Genet. 27, 135-141).

Ultraflo L and Celluclast 1.5 L are commercial enzyme compositions, and available from Novozymes A/S. Ultraflo L is derived from *Humicola insolens* and comprises cellulases and hemicellulases. Celluclast 1.5 L is derived from *Trichoderma reesei* and comprises cellobiohydrolases and endoglucanases.

Bio-Feed Wheat L is a commercial xylanase for feed application and available from Novozymes A/S. Bio-Feed Wheat L is derived from *Termomyces lanuginosus*.

Chemicals and Substrates

Arabinose and xylose were purchased from Merck (Darmstadt, Germany). Water soluble and water insoluble wheat arabinoxylans were obtained from Megazyme (Bray, County Wicklow, Ireland). The ethanol fermentation effluent, "vinasse", was provided by Tate & Lyle, Amylum UK (Greenwich, UK).

Soluble Wheat Arabinoxylan Substrate

Medium viscosity water-soluble wheat arabinoxylan was obtained from Megazyme (Bray, County Wicklow, Ireland). Monosaccharide contents after acid hydrolysis (0.4 N HCl, 2 h, 100° C.) and HPAEC were: Arabinose 275.8 mg/g, xylose 479.2 mg/g (=A:X 0.58), with only traces of galactose and glucose. According to the product sheet the starch, beta-glucan, protein, moisture, and ash contents by weight were <0.1%, <0.1%, 0.9%, 1.9%, and 2.2%, respectively.

Wheat Vinasse Substrate

Wheat vinasse, a by-product from industrial ethanol fermentation, was provided by Tate & Lyle, Amylum UK, (Greenwich, UK). The dry matter content of the vinasse was 9.02 wt %. Monosaccharide contents after acid hydrolysis (0.4 N HCl, 2 h, 100° C.) and HPAEC were: Arabinose 82.9 g/kg DM vinasse, xylose 119 g/kg DM vinasse mg/g, galactose 21.6 g/kg DM vinasse, and 78.2 g/kg DM vinasse. Organic acids, protein, ash, and ferulic acid constituted ~30%, ~16%, ~11%, and 0.2% by weight, respectively of the dry matter.

Preparation of Specific Arabinoxylan Polymers and Oligosaccharides

Doubly substituted arabinoxylan was prepared by incubating soluble wheat arabinoxylan (1 g) in 0.1 M acetate buffer (100 mL), pH 6.0 with 0.167 g α-L-arabinofuranosidase from *Meripilus giganteus* (GH51)·kg$^{-1}$ water soluble wheat arabinoxylan for 48 hours at 30° C. Singly substituted arabinoxylan was prepared by incubating water soluble wheat arabinoxylan (1 g) in 0.1 M acetate buffer (42 mL), pH 6.0 with 0.147 g α-L-arabinofuranosidase from *Humicola insolens* (GH43)·kg$^{-1}$ water soluble wheat arabinoxylan for 48 hours at 30° C. To halt the enzymatic reactions the mixtures were heated to 100° C. for 10 min. Arabinoxylan polymers were precipitated by addition of ethanol (126 ml). The precipitates were filtered (Miracloth) and dried in vacuum Oligosaccharides containing arabinosyl groups linked to terminal (1→3) were prepared by incubating the water insoluble wheat arabinoxylan (1 g) in 0.1 M acetate buffer (100 mL), pH 6.0 with 6.67 g Shearzyme (xylanase GH10)·kg$^{-1}$ water insoluble wheat arabinoxylan for 2 hours at 30° C. Oligosaccharides containing arabinosyl groups linked to internal (1→3) were prepared by incubating water insoluble wheat arabinoxylan (1 g) in 0.1 M acetate buffer (100 mL), pH 6.0 with 0.03 g Pentopan Mono (xylanase GH11)·kg$^{-1}$ water insoluble wheat arabinoxylan for 2 hours at 30° C. Oligosaccharides containing arabinosyl groups linked to internal (1→2) were prepared by incubating water insoluble wheat arabinoxylan (1 g) in 0.1 M acetate buffer (100 mL), pH 6.0 with 0.03 g Pentopan Mono (xylanase GH11)·kg$^{-1}$ water insoluble wheat arabinoxylan and alpha-L-arabinofuranosidase from *H. insolens* (GH43)·kg$^{-1}$ water soluble wheat arabinoxylan for 2 hours at 30° C. To halt the enzymatic reactions the mixtures were heated to 100° C. for 10 min. The arabinoxylo-oligosaccharides were concentrated on a rotary evaporator and evaluated by $^1$H-NMR.

Substrate Analysis

Contents of arabinose and xylose in arabinoxylan containing substrates were determined by acid hydrolysis with hydrochloric acid (0.4 N HCl, 2 hours, 100° C.) followed by HPAEC (Sørensen et al., 2003). All yields, including enzymatic hydrolysis yields, are reported as mg per g substrate dry matter or as relative yields in percent.

Assay for Activity Towards alpha-L-arabinofuranosidase Activity

Alpha-L-arabinofuranosidase activity may be assessed as described by Poutanen et al. (Appl. Microbiol. Biotechnol. 1988, 28, 425-432) using 5 mM p-nitrophenyl alpha-L-arabinofuranosidase as substrates. The reactions may be carried out in 50 mM citrate buffer at pH 6.0, 40° C. with a total reaction time of 30 min. The reaction is stopped by adding 0.5 ml of 1 M sodium carbonate and the liberated p-nitrophenol is measured at 405 nm. Activity is expressed in U/ml.

Assay for Alpha-arabinofuranosidase Activity on Di-substituted Arabinoxylan

Medium viscosity water-soluble wheat arabinoxylan (Megazyme, Bray, Ireland) was treated with an alpha-arabinofuranosidase of GH51 from *Meripilus giganteus* (SEQ ID NO:2) to remove single alpha-arabinofuranosyl substituents attached to the C(O)-3 arabinose of the arabinoxylan in order to produce an di-substituted arabinoxylan substrate with arabinofuranosyl substituents attached to both C(O)-2,3 of the xylose residues. The substrate was dialysed and freeze dried.

A 0.1% solution of the di-substituted arabinoxylan was prepared and the alpha-arabinofuranosidase activity was measured by mixing 0.1 ml enzyme, 0.9 ml buffer (0.12 M Succinic acid, pH 6.0) and 1.0 ml substrate solution in an eppendorf tube. The eppendorf tube was incubated at 60° C. for 1 hour with shaking. The amount of liberated arabinose was measured by HPAEC (high-performance anion-exchange chromatography).

HPAEC

Hydrolysates (10 µl) were applied onto a Dionex BioLC system fitted with a Dionex CarboPac™ PA1 guard column (4×250 mm) (Dionex Corporation, Sunnyvale, Calif., USA) combined with a CarboPac™ PA1 precolumn (4×50 mm). The monosaccharides were separated isocratically with 10 mM KOH for 15 min, flow: 1 mL·min$^{-1}$. Monosaccharides were detected by a pulsed electrochemical detector in the pulsed amperiometric detection mode. The potential of the electrode was programmed for +0.1 V (t=0-0.4 s) to -2.0 V (t=0.41-0.42 s) to 0.6 V (t=0.43 s) and finally -0.1 V (t=0.44-0.50 s), while integrating the resulting signal from t=0.2-0.4 s. A mixture of arabinose and xylose (concentration of each component: 0.0025-0.1 g·L$^{-1}$) was used as standard.

$^1$H-NMR Analysis

All degradation products were lyophilized twice from 99.9% $D_2O$ and re-dissolved in 99.9% $D_2O$. Some hydrolysates were dialyzed (Spectra/Por membrane molecular weight cut-off 1000) to remove free arabinose prior to the spectral analysis. The $^1$H-NMR spectra were recorded at 30° C. in a Varian Mercury-VX instrument operated at 400 MHz and equipped with a 4-nucleus auto-switchable probe. Data were collected over 128-512 scans and the HDO signal was used as a reference signal (4.67 ppm).

EXAMPLES

Example 1

Enzymatic Hydrolysis of Water-Insoluble Arabinoxylan

Water-insoluble wheat arabinoxylan substrate (0.05 g) dissolved in 50 ml double de-ionized water per assay (0.1% DM) was incubated with a composition of the invention, or with 10 wt % of a 50:50 mixture of Ultraflo and Celluclast 1.5 L. E/S relate to the weight of enzyme preparation (E) added in percent per weight of substrate (S).

The composition of the invention comprised 0.075 g GH51 alpha-arabinofuranosidase from *M. giganteus*/kg DM arabinoxylan, 0.075 g GH43 alpha-arabinofuranosidase from *H. insolens*/kg DM arabinoxylan, 0.075 g beta-xylosidase from *T. reesei*/kg DM arabinoxylan, and 0.075 g xylanase from *H. insolens*/kg DM arabinoxylan.

The treatments were performed for 24 hours at pH 5 and 50° C. Samples were withdrawn after 24 hours and immediately heated at 100° C. for 10 min. The samples were filtered (0.2 microM filter) and the levels of arabinose, and xylose were determined by HPAEC. Enzymatic hydrolysis experiments were performed in triplicate and the mean values reported are in percentage of the amounts released by acid hydrolysis. Results are presented in Table 1.

TABLE 1

Arabinose and xylose released from water insoluble wheat arabinoxylan by enzymatic hydrolysis. Numbers are in weight percent of the amount of each monosaccharide released by acid hydrolysis of the water-soluble wheat arabinoxylan samples.

| Enzyme | Arabinose | Xylose |
|---|---|---|
| Celluclast 1.5 L:Ultraflo L | 43 | 56.7 |
| Composition of the invention | 57 | 64 |

Enzymatic Hydrolysis of Water-Soluble Arabinoxylan

Water-soluble wheat arabinoxylan substrate (0.05 g) dissolved in 50 ml double de-ionized water per assay (0.1% DM) was incubated with a composition of the invention, or with 10 wt % of a 50:50 mixture of Ultraflo and Celluclast 1.5 L. E/S relate to the weight of enzyme preparation (E) added in percent per weight of substrate (S).

The composition of the invention comprised 0.080 g GH51 alpha-arabinofuranosidase from *M. giganteus*/kg DM arabinoxylan, 0.080 g GH43 alpha-arabinofuranosidase from *H. insolens*/kg DM arabinoxylan, 0.16 g beta-xylosidase from *T. reesei*/kg DM arabinoxylan, and 0.080 g xylanase from *H. insolens*/kg DM arabinoxylan.

The treatments were performed for 24 hours at pH 5 and 50° C. Samples were withdrawn after 24 hours and immediately heated at 100° C. for 10 min. The samples were filtered (0.2 microM filter) and the levels of arabinose, and xylose were determined by HPAEC. Enzymatic hydrolysis experiments were performed in triplicate and the mean values reported are in percentage of the amounts released by acid hydrolysis. Results are presented in Table 2.

TABLE 2

Arabinose and xylose released from water soluble wheat arabinoxylan by enzymatic hydrolysis. Numbers are in weight percent of the amount of each monosaccharide released by acid hydrolysis of the water-soluble wheat arabinoxylan samples.

| Enzyme | Arabinose | Xylose |
|---|---|---|
| Celluclast 1.5 L:Ultraflo L | 25 | 51 |
| Composition of the invention | 116 | 107 |

Example 2

The hydrolysis of vinasse was performed according to the method described for water soluble arabinoxylan in Example 1 except that the dosage of beta-xylosidase was 0.050 g/kg DM vinasse and the substrate level was 5 wt % DM. Samples were withdrawn after 24 h and heated immediately at 100° C. for 10 min to halt the enzyme reaction, centrifuged (14000 rpm, 10 min), filtered (0.2 microM filter) and subjected to HPAEC analysis to determine the levels of arabinose and xylose, see below. Enzymatic hydrolysis experiments were performed in duplicate and the mean values reported are in percentage of the amounts released by acid hydrolysis. Results are presented in Table 2.

TABLE 3

Arabinose and xylose released from vinasse by enzymatic hydrolysis. Numbers are in weight percent of the amount of each monosaccharide released by acid hydrolysis of the water-soluble wheat arabinoxylan samples.

| Enzyme | Arabinose | Xylose |
|---|---|---|
| Celluclast 1.5 L:Ultraflo L | 77 | 75 |
| Composition of the invention | 103 | 81 |

Example 3

Wheat arabinoxylan comprises arabinofuranoside as a monosubstituent linked to the 3-position of internal xylose and arabinofuranoside linked to the 3- and 2-position on di-substituted xylose, respectively. Substrates were produced comprising only one of the 3 types of arabinofuranoside linkages. The activity of the arabinofuranosidases towards these substrates was investigated.

TABLE 4

Activity on selected arabinoxylan polymers, incubation at pH 6, 40° C. for 2 hours.

| Substrate | Linkage | H. insolens (GH43) | Bifidobacterium adolescentis (GH43) | H. insolens (GH51) | M. giganteus (GH51) |
|---|---|---|---|---|---|
| Intact arabinoxylan | Mono-substituted (1→3) | — | — | x | xx |
|  | Di-substituted (1→2) | — | — | — | — |
|  | Di-substituted (1→3) | xx | x | — | — |
| Di-substituted arabinoxylan | Di-substituted (1→2) | — | — | — | — |
|  | Di-substituted (1→3) | xx | xx | — | — |
| Mono-substituted arabinoxylan | Mono-substituted (1→2) | — | — | xx | xx |
|  | Mono-substituted (1→3) | — | — | xx | xx | xx refers to more than 75% hydrolysis,
x(x) to 50-75% hydrolysis,
x to 25-50% hydrolysis and
(x) to 5-25% hydrolysis.
— refers to no detectable hydrolysis

Example 4

Soluble wheat arabinoxylan was incubated with 0.1 g enzyme protein per kg DM of alpha-L-arabinofuranosidase from *H. insolens* (GH43), *B. adolescentis* (GH43), *H. insolens* (GH51), and *M. giganteus* (GH51). The released arabinose as mg per g water soluble wheat arabinoxylan, their hypothetical sum, and their arabinose release after treatment with 0.2 g enzyme protein per kg DM of a 50:50 mixture of alpha-L-arabinofuranosidases from from *H. insolens* (GH43), *Bi.* sp. (GH43), *H. insolens* (GH51), and *M. giganteus* (GH51) was measured. Results are expressed as the average of triplicate determinations, coefficient of variation on mean<6.4.

TABLE 5

Released arabinose from soluble wheat arabinoxylan treated with alpha-L-arabinofuranosidase at two different temperature and pH conditions.

|  | pH 6, 40° C. | pH 5, 50° C. |
| --- | --- | --- |
| *H. insolens* (GH43) | 128.0 a | 147.0 a |
| *M. giganteus* (GH51) | 48.15 c | 121.0 b |
| *B. adolescentis* (GH43) | 63.43 b | 4.833 d |
| *H. insolens* (GH51) | 20.75 d | 18.47 c |

Values within a column not sharing a common letter index differ with statistical significance (P < 0.05).

TABLE 6

Released arabinose from soluble wheat arabinoxylan treated with 50%:50% mixtures of alpha-L-arabinofuranosidases at pH 5, 50° C.

|  | pH 5, 50° C. | pH 5, 50° C. |
| --- | --- | --- |
| *H. insolens* (GH43) and *H. insolens* (GH51) | — | 168.3 b |
| *H. insolens* (GH43) and *M. Giganteus* (GH51) | — | 289.0 a |
| *B. adolescentis* (GH43) and *H. insolens* (GH51) | — | 17.43 d |
| *B. adolescentis* (GH43) and *M. giganteus* (GH51) | — | 131.0 c |

Values within a column not sharing a common letter index differ with statistical significance (P < 0.05).

Example 5

Spent grain was obtained from a pilsner brewing process using hammer milled barley malt. The spent grain was freeze dried to a dry matter content of 96.1% w/w and milled. The spent grain material was suspended 5 g dry matter/100 ml succinic acid-sodium succinate buffer pH 5.0 and subjected to hydrolysis by two treatments: 1) a conventional treatment using a 50:50 mixture of Celluclast 1.5 L+Ultraflo L with 6.5 g enzyme protein per kg spent grain dry matter and 2) a treatment of the invention applying a 25:25:25:25 blend on protein weight basis of the GH43 alpha-L-arabinofuranosidase from *H. insolens* (SEQ ID NO:1), the GH51 alpha-L-arabinofuranosidase from *M. giganteus* (SEQ ID NO:2), the GH3 beta-xylosidase from *Trichoderma reesei* (SEQ ID NO:3) and the GH10 endo-1,4-beta-xylanase from *H. insolens* (SEQ ID NO:4). An enzyme dosage equivalent to 0.6 g enzyme protein per kg spent grain dry matter was used.

The hydrolysis was performed in Ependorfer tubes incubated in a Thermomixer Compact at 1000 rpm for 16 hours at 50° C. The samples were cooked for 10 minutes, centrifuged for 10 minutes at 14000×g and the soluble phase was analysed carbohydrates on HPLC. HPLC was performed on a Dionex BioLC using a GS50 Gradient Pump, AS50 Autosampler, and an ED40 Elektrochemical detector. The concentration of released arabinose and xylose was measured.

TABLE 7

Spent grain: Results of HPLC-analyses of released arabinose and xylose in g/litre.

|  | Arabinose | Xylose |
| --- | --- | --- |
| Control, no enzyme | 0.00 | 0.00 |
| 1) Conventional treatment | 1.19 | 1.98 |
| 2) Treatment of the invention | 1.48 | 2.12 |

Example 6

An arabinoxylan containing solution was obtained by cooking wheat straw at 190° C. followed by separating the liquid from the straw by filtration. In all experiments 1.5 g of the liquid was further diluted to 2.0 g by addition of acid/base for pH adjustment, by addition of enzyme solution and by addition of deionized water. The liquid was incubated with 2.5 g enzyme protein per liter reaction volume with either the enzyme mix of the invention, with the conventional cellulose blend consisting of a 50:50 mixture of Ultraflo and Celluclast 1.5 L (mix ratio based on protein content).

The composition of the invention comprised a 10:10:5:25 blend on protein weight basis of the alpha-arabinofuranosidase from *H. insolens* (SEQ ID NO:1), the alpha-arabinofuranosidase from *M. giganteus* (SEQ ID NO:2), the beta-xylosidase from *T. reesei* (SEQ ID NO:3) and the xylanase from *H. insolens* (SEQ ID NO:4). The treatments were performed for 24 hours at three pH levels (4, 5, 6) and at two temperatures (40, 50° C.). Samples were withdrawn after 24 hours and immediately heated at 100° C. for 10 min. The samples were filtered (0.2 microM filter) and the levels of arabinose, and xylose were determined by HPAEC. All Enzymatic hydrolysis experiments were performed in duplicate and the mean values reported are in percentage of the amounts released by acid hydrolysis. Results are presented in Table 8.

TABLE 8

Arabinose and xylose released from water soluble wheat arabinoxylan by enzymatic hydrolysis. Numbers are in weight percent of the amount of each monosaccharide released by acid hydrolysis of the water soluble wheat arabinoxylan.

|  |  | Arabinose | | Xylose | |
| --- | --- | --- | --- | --- | --- |
| Temperature [° C.] | pH | Reference | Invention | Reference | Invention |
| 40 | 4 | 63 | 95 | 66 | 72 |
| 40 | 5 | 70 | 91 | 71 | 78 |
| 40 | 6 | 76 | 94 | 79 | 88 |
| 50 | 4 | 60 | 93 | 71 | 72 |
| 50 | 5 | 66 | 92 | 81 | 88 |
| 50 | 6 | 87 | 99 | 87 | 87 |

The invention claimed is:

1. A process of hydrolyzing an arabinoxylan containing substrate comprising contacting the arabinoxylan containing substrate with:
   a) a GH51 alpha-L-arabinofuranosidase which has at least 90% sequence identity to the sequence of amino acids 1-627 of SEQ ID NO: 2, and
   b) a GH43 alpha-L-arabinofuranosidase.

2. The process of claim 1, wherein the GH51 alpha-L-arabinofuranosidase has at least 95% sequence identity to the sequence of amino acids 1-627 of SEQ ID NO: 2.

3. The process of claim 1, wherein the GH51 alpha-L-arabinofuranosidase has at least 97% sequence identity to the sequence of amino acids 1-627 of SEQ ID NO: 2.

4. The process of claim 1, wherein the GH51 alpha-L-arabinofuranosidase comprises the sequence of amino acids 1-627 of SEQ ID NO: 2.

5. The process of claim 1, wherein the GH43 alpha-L-arabinofuranosidase has at least 90% sequence identity to the sequence of amino acids 1-540 of SEQ ID NO: 1.

6. The process of claim 1, wherein the GH43 alpha-L-arabinofuranosidase has at least 95% sequence identity to the sequence of amino acids 1-540 of SEQ ID NO: 1.

7. The process of claim 1, wherein the GH43 alpha-L-arabinofuranosidase has at least 97% sequence identity to the sequence of amino acids 1-540 of SEQ ID NO: 1.

8. The process of claim 1, wherein the GH43 alpha-L-arabinofuranosidase comprises the sequence of amino acids 1-540 of SEQ ID NO: 1.

9. The process of claim 1, further comprising contacting the arabinoxylan containing substrate with
   a) a beta-xylosidase, and/or
   b) an endo-1,4-beta-xylanase.

10. The process of claim 9, wherein the beta-xylosidase is a GH3 beta-xylosidase.

11. The process of claim 9, wherein the endo-1,4-beta-xylanase is a GH10 or GH11 endo-1,4-beta-xylanase.

12. The process of claim 1, further comprising contacting the arabinoxylan containing substrate with an enzyme selected from the group consisting of acetyl xylan esterase, alpha-amylase, cellulase, CGTase, feruloyl esterase, beta-glucanase, glucoamylase, beta-glycosidase, phytase, and protease.

13. The process of claim 1, wherein the alpha-L-arabinofuranosidase of GH43 is present in an amount of at least 5% w/w of total enzyme protein.

14. The process of claim 13, wherein the alpha-L-arabinofuranosidase of GH43 is present in an amount of at least 10% w/w of total enzyme protein.

15. The process of claim 14, wherein the alpha-L-arabinofuranosidase of GH43 is present in an amount of at least 15% w/w of total enzyme protein.

16. A composition comprising:
   a) a GH51 alpha-L-arabinofuranosidase which has at least 90% sequence identity to the sequence of amino acids 1-627 of SEQ ID NO: 2, and
   b) a GH43 alpha-L-arabinofuranosidase.

17. The composition of claim 16, wherein the GH51 alpha-L-arabinofuranosidase has at least 95% sequence identity to the sequence of amino acids 1-627 of SEQ ID NO: 2.

18. The composition of claim 16, wherein the GH51 alpha-L-arabinofuranosidase has at least 97% sequence identity to the sequence of amino acids 1-627 of SEQ ID NO: 2.

19. The composition of claim 16, wherein the GH51 alpha-L-arabinofuranosidase comprises the sequence of amino acids 1-627 of SEQ ID NO: 2.

20. The composition of claim 16, wherein the GH43 alpha-L-arabinofuranosidase has at least 90% sequence identity to the sequence of amino acids 1-540 of SEQ ID NO: 1.

21. The composition of claim 16, wherein the GH43 alpha-L-arabinofuranosidase has at least 95% sequence identity to the sequence of amino acids 1-540 of SEQ ID NO: 1.

22. The composition of claim 16, wherein the GH43 alpha-L-arabinofuranosidase has at least 97% sequence identity to the sequence of amino acids 1-540 of SEQ ID NO: 1.

23. The composition of claim 16, wherein the GH43 alpha-L-arabinofuranosidase comprises the sequence of amino acids 1-540 of SEQ ID NO: 1.

24. The composition of claim 16, which further comprises:
   a) a beta-xylosidase and/or
   b) an endo-1,4-beta-xylanase.

25. The composition of claim 24, wherein the beta-xylosidase is a GH3 beta-xylosidase.

26. The composition of claim 24, wherein the endo-1,4-beta-xylanase is a GH10 or GH11 endo-1,4-beta-xylanase.

27. The composition of claim 16, which further comprises one or more enzymes selected from the group consisting of acetyl xylan esterase, alpha-amylase, cellulase, feruloyl esterase, CGTase, beta-glucanase, glucoamylase, beta-glycosidase, phytase, and protease.

28. The composition of claim 27, wherein the cellulase is a cellobiohydrolase.

* * * * *

SEQUENCE LISTING

<160> NUMBER OF SEQ ID NOS: 4

<210> SEQ ID NO 1
<211> LENGTH: 558
<212> TYPE: PRT
<213> ORGANISM: Humicola insolence
<220> FEATURE:
<221> NAME/KEY: mat_peptide
<222> LOCATION: (19)..(558)

<400> SEQUENCE: 1

Met Leu Gly Leu Lys Val Leu Cys Leu Ser Ala Val Val Gly Thr Ala
            -15                 -10                  -5

Val Ser Val Pro His Ala Gly Asn Leu Pro Arg Gln Ala Ser Thr Phe
    -1   1              5                  10

Thr Asn Pro Val Leu Trp Glu Asp His Pro Asp Leu Glu Val Phe Arg
 15              20                  25                      30

Val Gly Ser Val Phe Tyr Tyr Ser Ser Thr Phe Ala Tyr Ser Pro
                 35                  40                  45

Gly Ala Pro Val Leu Lys Ser Tyr Asp Leu Val His Trp Thr Pro Val
             50                  55                  60

Thr His Ser Val Pro Arg Leu Asn Phe Gly Ser Asn Tyr Asp Leu Pro
             65                  70                  75

Ser Gly Thr Pro Gly Ala Tyr Val Lys Gly Ile Trp Ala Ser Thr Leu
 80                  85                  90

Arg Tyr Arg Arg Ser Asn Asp Arg Phe Tyr Trp Tyr Gly Cys Val Glu
 95                 100                 105                    110

Gly Arg Thr Tyr Leu Trp Thr Ser Pro Gly Gly Asn Ala Leu Ala Asn
                115                 120                 125

Asn Gly Glu Val Pro Pro Ser Ala Trp Asn Trp Gln His Thr Ala Thr
             130                 135                 140

Ile Asp Asn Cys Tyr Tyr Asp Ala Gly Leu Leu Ile Asp Asp Asp Asp
                 145                 150                 155

Thr Met Tyr Ile Ala Tyr Gly Asn Pro Thr Ile Asn Val Ala Gln Leu
    160                 165                 170

Ser Pro Asp Gly Thr Arg Gln Val Arg Val Gln Gln Arg Val Tyr Ala
175                 180                 185                 190

His Pro Gln Gly Gln Thr Val Glu Gly Ala Arg Met Tyr Lys Ile Arg
                195                 200                 205

Gly Asn Tyr Tyr Ile Leu Val Thr Arg Pro Ala Asp Ala Glu Tyr Val
             210                 215                 220

Leu Arg Ser Thr Thr Gly Ser Pro Phe Gly Pro Tyr Glu Ala Arg Thr
225                 230                 235

Leu Val Ser Arg Ile Gln Gly Pro Leu Ala Asn Ala Gly Phe Ala His
    240                 245                 250

Gln Gly Gly Ile Val Asp Ala Pro Asp Gly Thr Trp His Tyr Val Ala
255                 260                 265                 270

Phe Met Asp Ala Tyr Pro Gly Gly Arg Ile Pro Val Ala Pro Leu
                275                 280                 285

Arg Trp Thr Ala Asp Gly Trp Pro Glu Val Val Thr Asp Ser Gln Gly
                290                 295                 300

Arg Trp Gly Thr Ser Tyr Pro Ile Pro Val Arg Gly Ala Lys Asn Ala
            305                 310                 315

Thr Glu Gly Leu Ala Ser Thr Asp Leu Asp Glu Phe Arg Gly Thr Arg
 320                 325                 330

```
Phe Ser Glu His Trp Glu Trp Asn His Asn Pro Asp Thr Ser Lys Phe
335                 340                 345                 350

Thr Leu Leu Gly Gly Asn Glu Gly Gly Leu Ile Leu Arg Thr Ala Thr
                355                 360                 365

Val Thr Gly Asp Leu Phe Ala Ala Arg Asn Thr Leu Thr Arg Arg Ile
            370                 375                 380

Ala Gly Pro Lys Ala Ser Gly Ile Phe Arg Leu Asp Val Arg Gly Met
                385                 390                 395

Arg Asp Gly Asp Arg Ala Gly Ala Val Leu Phe Arg Asp Arg Ala Ala
            400                 405                 410

Tyr Ile Gly Val Trp Lys Gln Gly Asn Glu Ala Arg Ile Val Met Val
415                 420                 425                 430

Asp Asp Leu Arg Leu Asn Glu Asp Gly Trp Arg Thr Ala Ser Thr Gly
                435                 440                 445

Arg Val Ala Ala Asn Gly Pro Val Ile Asp Thr Asn Ala Gln Gln Asp
            450                 455                 460

Ile Trp Leu Arg Ile Asp Ala Asp Ile Thr Pro Ala Phe Gly Thr Asn
                465                 470                 475

Thr Glu Arg Thr Thr Thr Phe Tyr Tyr Ser Ile Asp Gly Gly Arg Thr
            480                 485                 490

Tyr Thr Arg Leu Gly Pro Ala Phe Ala Met Thr Asn Ser Trp Arg Tyr
495                 500                 505                 510

Phe Thr Gly Tyr Arg Phe Gly Val Phe Asn Phe Ser Thr Lys Ser Leu
                515                 520                 525

Gly Gly Glu Val Lys Val Lys Gly Phe Lys Met Asn Met Ile
            530                 535                 540

<210> SEQ ID NO 2
<211> LENGTH: 643
<212> TYPE: PRT
<213> ORGANISM: Meripilus giganteus
<220> FEATURE:
<221> NAME/KEY: mat_peptide
<222> LOCATION: (17)..(643)

<400> SEQUENCE: 2

Met Lys Leu Leu Phe Leu Leu Gly Ala Phe Val Ala Gln Cys Leu Ala
        -15                 -10                 -5              -1

Val Thr Val Thr Val Asn Lys Asn Pro Ser His Thr Val Pro Ser Thr
1                   5                   10                  15

Leu Tyr Gly Leu Met Phe Glu Asp Ile Asn His Ser Gly Asp Gly Gly
            20                  25                  30

Leu Tyr Ala Glu Leu Leu Gln Asn Arg Ala Phe Gln Gln Val Thr Pro
        35                  40                  45

Asn Thr Ala Ala Ala Leu Ala Ala Trp His Pro Ile Ser Asn Ala Lys
50                  55                  60

Leu Ala Val Ile Gln Asp Pro Ser Pro Val Ser Asn Ala Leu Pro Asn
65                  70                  75                  80

Ser Leu Gln Phe Ser Val Pro Ser Gly Ser Gly Arg Val Gly Phe
            85                  90                  95

Thr Asn Glu Gly Phe Trp Gly Ile Lys Val Asp Ser Thr Trp Thr Tyr
        100                 105                 110

Lys Ala Ser Leu Phe Phe Arg Phe Pro Thr Ser Ser Ser Phe Ser Gly
            115                 120                 125

Ala Leu Thr Val Gly Leu Gln Thr Asn Ala Gly Arg Val Leu Ala Gln
        130                 135                 140
```

-continued

```
Asn Ser Thr Gln Ile Arg Gly Thr Thr Thr Lys Trp Thr Gln Ile Asn
145                 150                 155                 160
Leu Glu Leu His Pro Thr Ala Ser Ala Pro Asp Val Ser Asn Ser Phe
            165                 170                 175
Phe Val Thr Ile Asp Gly Ala Ala Gly Ala Gly Gln Thr Ile Asn Phe
            180                 185                 190
Ala Met Phe Ser Leu Phe Pro Pro Thr Phe Lys Asn Arg Pro Asn Gly
            195                 200                 205
Leu Arg Ala Asp Ile Ala Glu Thr Leu Ala Glu Met Gly Pro Ser Phe
            210                 215                 220
Phe Arg Phe Pro Gly Gly Asn Asn Leu Glu Gly Gln Thr Thr Ala Thr
225                 230                 235                 240
Arg Trp Gln Trp Asn Ala Thr Val Gly Ser Leu Leu Asp Arg Pro Gly
                245                 250                 255
Arg Val Gly Asp Trp Gly Tyr Val Asn Thr Asp Gly Leu Gly Leu Leu
                260                 265                 270
Glu Tyr Leu Gln Phe Phe Glu Asp Thr Gly Met Glu Pro Ile Met Ala
            275                 280                 285
Val Trp Ala Gly Tyr Ser Leu Gly Gly Thr Ser Leu Ala Glu Asn Gln
            290                 295                 300
Leu Ala Pro Tyr Ile Gln Gln Ala Ile Asp Gln Ile Asn Phe Val Ile
305                 310                 315                 320
Gly Asp Pro Ala Lys Ser Ala Pro Ala Ala Leu Arg Ala Ser Leu Gly
                325                 330                 335
His Pro Glu Pro Phe Thr Leu Arg Phe Val Glu Val Gly Asn Glu Asp
            340                 345                 350
Phe Phe Ala Ala Gly Ser Tyr Pro Tyr Arg Trp His Asp Phe Val Thr
            355                 360                 365
Ala Leu Gln Ala Gln Phe Pro Gln Ile Arg Phe Ile Ala Thr Thr Asn
            370                 375                 380
Ala Trp Asn Pro Val Leu Ser Pro Val Pro Gln Ser Tyr Asp Val His
385                 390                 395                 400
Val Tyr Gln Thr Pro Thr Trp Phe Tyr Gln Asn Ala Phe Tyr Tyr Asp
                405                 410                 415
Gly Phe Gln Arg Asn Gly Thr Thr Tyr Phe Glu Gly Tyr Ala Ala
                420                 425                 430
Ile Ser Thr Asn Ala Asn Asp Leu Phe Gly Thr Val Ala Asp Gly Arg
            435                 440                 445
Leu Ala Phe Pro Thr Val Gln Ser Ala Thr Gly Glu Ala Ala Phe Met
450                 455                 460
Thr Gly Leu Glu Arg Asn Ser Asp Ile Val Phe Ala Ala Ser Tyr Ala
465                 470                 475                 480
Pro Leu Leu Gln His Val Asn Ser Thr Gln Trp Thr Pro Asp Leu Val
            485                 490                 495
Ser Tyr Asp Ala Gly Ser Val Ile Lys Ser Thr Ser Phe Phe Ala Gln
            500                 505                 510
Lys Leu Phe Ala Leu Asn Lys Gly Asp Gln Tyr Leu Pro Ser Thr Leu
            515                 520                 525
Pro Thr Asn Gly Gly Thr Leu His Trp Ser Ile Thr Arg Ala Ser Ser
            530                 535                 540
Ser Gly Lys Thr Phe Ile Lys Ile Ala Asn Ala Gly Ser Ser Ala Gln
545                 550                 555                 560
Ser Leu Thr Phe Gln Leu Thr Gln Phe Asn Ser Val Ser Ser Thr Gly
```

```
                  565                 570                 575
Thr Leu Gln Val Leu Thr Gly Pro Glu Thr Ala Ser Asn Thr Pro Glu
                580                 585                 590
Ala Pro Gln Ala Ile Val Pro Lys Thr Ser Thr Ile Gly Thr Gly Lys
                595                 600                 605
Thr Phe Thr Tyr Asn Ala Pro Ala Phe Ser Val Ser Val Ile Thr Val
                610                 615                 620
Thr Thr Asn
625

<210> SEQ ID NO 3
<211> LENGTH: 797
<212> TYPE: PRT
<213> ORGANISM: Trichoderma reesei
<220> FEATURE:
<221> NAME/KEY: mat_peptide
<222> LOCATION: (1)..(797)

<400> SEQUENCE: 3

Met Val Asn Ala Ala Leu Ala Ala Leu Ser Ala Leu Leu Pro
1               5                  10                  15
Thr Ala Leu Ala Gln Asn Asn Gln Thr Tyr Ala Asn Tyr Ser Ala Gln
                20                  25                  30
Gly Gln Pro Asp Leu Tyr Pro Glu Thr Leu Ala Thr Leu Thr Leu Ser
                35                  40                  45
Phe Pro Asp Cys Glu His Gly Pro Leu Lys Asn Asn Leu Val Cys Asp
            50                  55                  60
Ser Ser Ala Gly Tyr Val Glu Arg Ala Gln Ala Leu Ile Ser Leu Phe
65                  70                  75                  80
Thr Leu Glu Glu Leu Ile Leu Asn Thr Gln Asn Ser Gly Pro Gly Val
                85                  90                  95
Pro Arg Leu Gly Leu Pro Asn Tyr Gln Val Trp Asn Glu Ala Leu His
                100                 105                 110
Gly Leu Asp Arg Ala Asn Phe Ala Thr Lys Gly Gly Gln Phe Glu Trp
            115                 120                 125
Ala Thr Ser Phe Pro Met Pro Ile Leu Thr Thr Ala Ala Leu Asn Arg
130                 135                 140
Thr Leu Ile His Gln Ile Ala Asp Ile Ile Ser Thr Gln Ala Arg Ala
145                 150                 155                 160
Phe Ser Asn Ser Gly Arg Tyr Gly Leu Asp Val Tyr Ala Pro Asn Val
                165                 170                 175
Asn Gly Phe Arg Ser Pro Leu Trp Gly Arg Gly Gln Glu Thr Pro Gly
                180                 185                 190
Glu Asp Ala Phe Phe Leu Ser Ser Ala Tyr Thr Tyr Glu Tyr Ile Thr
            195                 200                 205
Gly Ile Gln Gly Gly Val Asp Pro Glu His Leu Lys Val Ala Ala Thr
        210                 215                 220
Val Lys His Phe Ala Gly Tyr Asp Leu Glu Asn Trp Asn Asn Gln Ser
225                 230                 235                 240
Arg Leu Gly Phe Asp Ala Ile Ile Thr Gln Gln Asp Leu Ser Glu Tyr
                245                 250                 255
Tyr Thr Pro Gln Phe Leu Ala Ala Arg Tyr Ala Lys Ser Arg Ser
                260                 265                 270
Leu Met Cys Ala Tyr Asn Ser Val Asn Gly Val Pro Ser Cys Ala Asn
            275                 280                 285
Ser Phe Phe Leu Gln Thr Leu Leu Arg Glu Ser Trp Gly Phe Pro Glu
```

```
            290                 295                 300
Trp Gly Tyr Val Ser Ser Asp Cys Asp Ala Val Tyr Asn Val Phe Asn
305                 310                 315                 320

Pro His Asp Tyr Ala Ser Asn Gln Ser Ala Ala Ser Ser Leu
                    325                 330             335

Arg Ala Gly Thr Asp Ile Asp Cys Gly Gln Thr Tyr Pro Trp His Leu
                340                 345                 350

Asn Glu Ser Phe Val Ala Gly Glu Val Ser Arg Gly Glu Ile Glu Arg
            355                 360                 365

Ser Val Thr Arg Leu Tyr Ala Asn Leu Val Arg Leu Gly Tyr Phe Asp
370                 375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Val Arg Ser Ile
            420                 425                 430

Ala Leu Ile Gly Pro Trp Ala Asn Ala Thr Thr Gln Met Gln Gly Asn
            435                 440                 445

Tyr Tyr Gly Pro Ala Pro Tyr Leu Ile Ser Pro Leu Glu Ala Ala Lys
450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Lys Lys Ser
            485                 490                 495

Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
            515                 520                 525

Ile Lys Gln Leu Ser Glu Val Gly Lys Pro Leu Val Val Leu Gln Met
530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
            595                 600                 605

Met Asn Leu Arg Pro Asp Gly Lys Ser Asn Pro Gly Gln Thr Tyr Ile
610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
            675                 680                 685

Lys Thr Glu Ser Pro Tyr Thr Ala Met Leu Phe Val Arg Thr Ser Asn
            690                 695                 700

Ala Gly Pro Ala Pro Tyr Pro Asn Lys Trp Leu Val Gly Phe Asp Arg
705                 710                 715                 720
```

```
Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
        755                 760                 765

Leu Glu Phe Glu Leu Val Gly Glu Val Thr Ile Glu Asn Trp Pro
    770                 775                 780

Leu Glu Glu Gln Gln Ile Lys Asp Ala Thr Pro Asp Ala
785                 790                 795

<210> SEQ ID NO 4
<211> LENGTH: 389
<212> TYPE: PRT
<213> ORGANISM: Humicola insolens
<220> FEATURE:
<221> NAME/KEY: mat_peptide
<222> LOCATION: (17)..(389)

<400> SEQUENCE: 4

Met Arg Ser Ile Ala Leu Ala Leu Ala Ala Pro Ala Val Leu Ala
    -15                 -10                 -5                  -1

Gln Ser Gln Leu Trp Gly Gln Cys Gly Gly Ile Gly Trp Asn Gly Pro
1                5                   10                  15

Thr Thr Cys Val Ser Gly Ala Thr Cys Thr Lys Ile Asn Asp Trp Tyr
            20                  25                  30

His Gln Cys Leu Pro Gly Gly Asn Asn Asn Pro Pro Ala Thr
        35                  40                  45

Thr Ser Gln Trp Thr Pro Pro Ala Gln Thr Ser Ser Asn Pro Pro
50                  55                  60

Pro Thr Gly Gly Gly Gly Asn Thr Leu His Glu Lys Phe Lys Ala
65                  70                  75                  80

Arg Gly Lys Gln Tyr Phe Gly Thr Glu Ile Asp His Tyr His Leu Asn
            85                  90                  95

Asn Asn Gln Leu Met Glu Ile Ala Arg Arg Glu Phe Gly Gln Ile Thr
            100                 105                 110

His Glu Asn Ser Met Lys Trp Asp Ala Thr Glu Pro Ser Arg Gly Ser
        115                 120                 125

Phe Ser Phe Gly Asn Ala Asp Arg Val Val Asp Trp Ala Thr Ser Asn
130                 135                 140

Gly Lys Leu Ile Arg Gly His Thr Leu Leu Trp His Ser Gln Leu Pro
145                 150                 155                 160

Gln Trp Val Gln Asn Ile Asn Asp Arg Asn Thr Leu Thr Gln Val Ile
            165                 170                 175

Glu Asn His Val Arg Thr Val Met Thr Arg Tyr Lys Gly Lys Ile Phe
        180                 185                 190

His Tyr Asp Val Val Asn Glu Ile Leu Asp Glu Asn Gly Gly Leu Arg
    195                 200                 205

Asn Ser Val Phe Ser Arg Val Leu Gly Glu Asp Phe Val Gly Ile Ala
210                 215                 220

Phe Arg Ala Ala Arg Ala Ala Asp Pro Asp Ala Lys Leu Tyr Ile Asn
225                 230                 235                 240

Asp Tyr Asn Leu Asp Ser Ala Asn Tyr Ala Lys Thr Arg Gly Met Ile
            245                 250                 255

Asn Leu Val Asn Lys Trp Val Ser Gln Gly Val Pro Ile Asp Gly Ile
            260                 265                 270
```

-continued

```
Gly Thr Gln Ala His Leu Ala Gly Pro Gly Gly Trp Asn Pro Ala Ser
    275                 280                 285

Gly Val Pro Ala Ala Leu Gln Ala Leu Ala Gly Ala Asn Val Lys Glu
    290                 295                 300

Val Ala Ile Thr Glu Leu Asp Ile Gln Gly Ala Gly Ala Asn Asp Tyr
305                 310                 315                 320

Val Thr Val Ala Asn Ala Cys Leu Asn Val Gln Lys Cys Val Gly Ile
                325                 330                 335

Thr Val Trp Gly Val Ser Asp Arg Asp Thr Trp Arg Ser Asn Glu Asn
            340                 345                 350

Pro Leu Leu Tyr Asp Arg Asp Tyr Arg Pro Lys Ala Ala Tyr Asn Ala
        355                 360                 365

Leu Met Asn Ala Leu
    370
```